United States Patent
Adler et al.

[11] Patent Number: 6,009,146
[45] Date of Patent: Dec. 28, 1999

[54] MEVSCAN TRANSMISSION X-RAY AND X-RAY SYSTEM UTILIZING A STATIONARY COLLIMATOR METHOD AND APPARATUS

[76] Inventors: Richard J. Adler, 4421 McLeod Rd., NE., Suite A, Albuquerque, N.Mex. 87109; Martin Annis, 12 Ellot St., Cambridge, Mass. 02138-5706

[21] Appl. No.: 08/880,927

[22] Filed: Jun. 23, 1997

[51] Int. Cl.⁶ ................................................. G01N 23/04
[52] U.S. Cl. .......................................... 378/98.6; 378/137
[58] Field of Search .............................. 378/98.6, 62, 65, 378/41, 137, 149, 143

[56] References Cited

U.S. PATENT DOCUMENTS

| | | | |
|---|---|---|---|
| 3,780,291 | 12/1973 | Stein et al. | 250/363 |
| 3,962,579 | 6/1976 | Winnek | 378/41 |
| 4,181,839 | 1/1980 | Hatton et al. | 378/41 X |
| 4,281,251 | 7/1981 | Cleland et al. | 250/398 |
| 4,521,900 | 6/1985 | Rand | 378/137 |
| 5,124,658 | 6/1992 | Adler | 328/233 |
| 5,267,294 | 11/1993 | Kuroda et al. | 378/137 X |
| 5,339,347 | 8/1994 | Slatkin et al. | 378/149 X |
| 5,712,889 | 1/1998 | Lanzara et al. | 378/137 X |

OTHER PUBLICATIONS

"Varian Linatron—High Energy X–Ray Applications for Nondestructive Testing", pp. 26–27 (no date given on publication).

"Energy–Beam Processing of Materials", Taniguchi, Clarendon Press, Oxford, pp. 19–21, 1989.

*Primary Examiner*—David P. Porta
*Attorney, Agent, or Firm*—Dennis F. Armijo; Donovan F. Duggan

[57] ABSTRACT

High energy scanning apparatus including a high voltage electrostatic generator and particle accelerator. A variable-trajectory electron beam is converted to a photon beam and collimated by a stationary collimator having a plurality of photon-passing slits. The stationary collimator produces a plurality of photon beams linearly and angularly displaced relative to each other in two dimensions. The photon beams are detected, thereby producing a plurality of preselected images including stereoscopic images. Also disclosed is a method of using the apparatus.

23 Claims, 5 Drawing Sheets

MEVSCAN TRANSMISSION X-RAY AND X-RAY SYSTEM UTILIZING A STATIONARY COLLIMATOR METHOD AND APPARATUS

BACKGROUND OF THE INVENTION

1. Field of the Invention (Technical Field)

The present invention relates to a scanning x-ray apparatus operating with a peak x-ray energy of up to or greater than 1 MeV; and a method of using such apparatus.

2. Background Art

X-ray transmission images are widely used in modern technology including their use in medical imaging, nondestructive testing of industrial equipment, and for the inspection of cargo and baggage for contraband.

X-ray images—both transmission and scattered—are normally made from x-ray sources, which are fixed in space and as small as possible in area. The x-rays are produced by the impact of a beam of electrons on a target. This necessitates high power density of electrons on the target. The spatial resolution and contrast of x-ray images are dependent upon the size of the x-ray source, the x-ray signal level and the x-ray signal-to-noise ratio.

Further, as set forth in "Varian Linatron—High Energy X-Ray Applications for Nondestructive Testing", pp 26–27 (no date given on publication), Varian Associates, Palo Alto, Calif., image quality requires sharpness and high contrast to assure good radiographic quality. The primary sources of unsharpness in radiography are inherent unsharpness, $U_i$, and geometric unsharpness, $U_g$, which is defined by the expression:

$$U_g = S/\{D/T\}, \qquad (1)$$

where

S=source spot diameter,

D=distance from the source spot to the object,

T=thickness of the object.

Source spot size is thus critical to image quality. Heating which can lead to melting of the target limits the ratio of source spot diameter, S, to the power, P, to a practical value of $$P/S < 1 \text{ kw/mm}. \qquad (2)$$

Thus, for P=1 kW, the minimum source diameter, S, is 1 mm; for P=4 kW the S must be at least 4 mm. The reason for this limitation is the fundamental heat transfer capability of high temperature materials as described in "Energy-Beam Processing of Materials", Taniguchi, Clarendon Press, Oxford, pp 19–21, 1989. Equipment which intrinsically embodies this power limitation in conjunction with it's means of producing an X-ray pencil beam and X-ray image, is described in J. A. Stein and R. Swift, U.S. Pat. No. 3,780,291. In that device, the X-rays are produced by an X-Ray tube in which the flux of X-rays is limited by the heating of the anode of the X-Ray tube.

One prior art device used in overcoming this limitation is to move the x-ray target material rapidly in front of the electron beam while keeping the electron beam in a fixed location, as in the well-known "rotating anode" x-ray source. Another prior art embodied in U.S. Pat. No. 4,521,900 to Rand, is used for tomographic scanning at lower energies of the electron beam and moves the electron beam by deflection.

No prior art, however, suggests using a moving x-ray beam in conjunction with a stationary collimator to produce a moving pencil beam of x-rays, as described in the current invention. The moving pencil beam of x-rays is then used to produce an x-ray image. The moving pencil beam of x-rays is produced by changing the trajectory of an electron beam magnetically such that the intersection of the electron beam with the target material moves in a pre-selected manner across the target material. The motion of the beam may be in a manner similar to that suggested in U.S. Pat. No. 4,281,251 to Cleland and Thompson.

The significance of X-ray flux to X-ray imaging is elucidated by understanding the limits of X-ray imaging of thick materials. The fundamental limit to x-ray imaging through thick materials is determined by the number of photons which exit the material and are detected by the detector, and the ratio of this number to the number of "background" or equivalent noise photons produced in the detector in the same time interval. As a rule-of-thumb, the number of photons required to image a pixel (the minimum area detected in the x-ray image) is 5 times background. If there is much less than 1 background photon/pixel, 5 photons per pixel are required to make a good image.

The transmitted photon flux, $F_t$, in a "good" geometry system (one which is not limited by scattered radiation) such as that defined by pencil beam imaging is given by:

$$F_t = F_0 * \exp(-Z^* \mu), \qquad (3)$$

where

Z=the thickness of the material penetrated (g/cm²) normalized to the density $\mu$=the mass attenuation coefficient of the penetrated material (cm²/g).

If $F_{tmin}$ is the minimum detectable photon flux, the maximum thickness of material which can be penetrated is:

$$Z_{wax} = [ln(F_0/F_{tmin})]/\mu \qquad (4)$$

Several factors determine $F_0$ including, 1) the power of the accelerator, 2) the maximum amount of electron power which can be incident on the target without melting it, and 3) the distance between the x-ray source location and the material being penetrated.

$F_0$ is proportional to the electron beam power for fixed beam energy, and $F_0$ increases as (beam energy)$^{(1,8)}$, for fixed beam power. $\mu$ varies slowly with x-ray photon energy, slowly decreasing with higher energies. The value of $F_o$ also varies inversely with distance squared from the point source. The valuable result is a technique which allows one to place the source closer to the object. Because high energy x-ray sources produce a relatively small angle cone of emission, the distance from a point x-ray source to the object must be greater than the projected dimension of the object in a conventional prior art point source x-ray system such as the system described in the '291 patent of Stein and Swift. In the present invention, using a high energy electrostatic generator and particle accelerator such as that disclosed in U.S. Pat. No. 5,124,658, to Adler, entitled *Nested High Voltage Generator/Particle Accelerator*, the electron beam intersects the target along a line (by differing trajectories) reducing the average power per unit area on the x-ray target by a factor of more than 100 for a typical object with a projected dimension of 10'. Thus $F_0$ may be increased by a factor of 100 without melting the target. Using equation 4, assuming water as the absorbing material, and an average x-ray photon energy of 1 MeV, the penetration, Z, may be increased by 70 cm (27") without melting the target.

Alternatively where fine inspections are required, the x-ray spot size may be reduced without a dramatic decrease in power of the x-ray source which would take place in conventional X-Ray tubes.

The ability to move the x-ray source close to the object results from the fact that the collimator does not need to converge on a point source of X-ray radiation. Instead, the source becomes a line of radiation which is unique to the present invention, compared to prior art "point" source systems. This property leads to an increase of incident photon flux, $F_0$, of 4 to 40 times, thereby enabling an increase of penetration of $1.4/\mu$ to $3.7/\mu$. Using the same example as above, corresponds to an increase of penetration through an object consisting mainly of water of 21 cm to 55 cm (8" to 22").

Because the electron beam has no mechanical inertia, in contrast to the prior art which uses mechanically moving collimators, it is possible to instantaneously speed up, slow down, or discontinuously move the beam from one point on the target line to another one. This feature allows different portions of the object with widely different thickness to receive different incident x-ray fluxes. This "Smart Imaging" can be accomplished automatically by using the signal recorded in the detector in a feedback loop to the deflecting coils which determine the position of the electron beam. In one embodiment, "Smart Imaging" can be used to set the level of measured photon flux to a fixed level with the desired signal to noise level, and the X-ray beam will dwell at each location long enough to generate the fixed level of photon flux before moving on. In this embodiment the attenuation is inversely proportional to the dwell time. An attractive feature of this embodiment is that the stray radiation generated is the minimum possible for a given signal to noise ratio and photon flux. A second attractive feature of this embodiment is that the data recording system can be greatly simplified. For example, a 4 bit digitizer or an analog comparator supplemented by a single time measurement device could be used to replace a 16 bit digitizer. The lateral motion and additional scans are in general produced by moving the object to be imaged by a stationary MeVScan device with the MeVScan device producing a line of the image. Sequential lines of the image are produced by repetitive scans of the object as moved by a conveyor, or the like, and taken at sequential times.

SUMMARY OF THE INVENTION
(DISCLOSURE OF THE INVENTION)

In accordance with the present invention there is provided a scanning X ray apparatus and method. The preferred scanning apparatus comprises a high energy electrostatic generator and particle accelerator for producing a high energy electron beam, programmable magnet(s) for pre-selectively varying the trajectory of the electron beam, a target for converting the electron beam into a photon beam, a stationary collimator comprising a plurality of groups of slits linearly and angularly offset from each other in two dimensions, for collimating said photon beam into a pencil beam or plurality of pencil beams and at least one transmission detector for detecting the collimated pencil photon beam, whereby a plurality of preselected images, including stereoscopic images, are thereby produced.

The apparatus 1 further comprises an X-ray transmission detector for detecting backscattered X-rays, whereby the backscattered images are converted into an image. The preferred preselected images and backscattered images are produced simultaneously.

The apparatus can further comprise an apparatus for moving the object to be scanned in a predetermined direction and speed.

The preferred high energy scanning method comprises the steps of producing a high energy electron beam, converting the electron beam into a photon beam and collimating the photon beam and thereby producing a preselected pattern of linearly and angularly offset pencil-like photon beams. The step of producing a high energy electron beam further comprises the step of providing a high energy electrostatic generator and particle accelerator.

The step of converting the electron beam into a photon beam further comprises the step of pre-selectively varying the trajectory of the electron beam. The step of converting the electron beam into a photon beam can further comprise the step of providing an X-ray conversion target. The step of converting the electron beam into the photon beam can further comprise the step of providing a target of gold-plated on aluminum. The step of collimating the photon beam can further comprise the step of providing a stationary collimator having a plurality of slits for producing the pencil-like photon beams.

The step of providing a stationary collimator having a plurality of slits can further comprise the step of providing a plurality of linearly and angularly offset groups of slits. The alternative method can further comprise the step of providing a plurality of linearly and angularly offset groups of slits offset from each other in two dimensions.

The preferred method further comprises the step of detecting the pencil-like photon beams, whereby a plurality of preselected images, including stereoscopic images, are produced. The alternative method further comprises the step of detecting backscattered X-rays whereby backscattered images are produced. The method comprises simultaneously producing the plurality of preselected images and backscattered images. The method can also comprise the step of moving the object to be scanned in a predetermined direction and speed.

The preferred high energy scanning apparatus comprises an apparatus for producing a high energy electron beam, structure for converting said electron beam into a photon beam and an apparatus for collimating said photon beam and thereby producing a preselected pattern of linearly and angularly offset pencil-like photon beams. The apparatus for producing a high energy electron beam comprises megavolt electrostatic generator and particle accelerator. The structure for converting the electron beam into a photon beam further comprises an apparatus for preselectively varying the trajectory of the electron beam. The structure for converting the electron beam into the photon beam can also comprise a tungsten emitter. The structure for converting the electron beam into the photon beam can also comprise a gold-plated aluminum emitter. The apparatus for collimating the photon beam preferably comprises a stationary collimator having a plurality of slits for producing the pencil-like photon beams. The preferred plurality of slits further comprises a plurality of linearly and angularly offset groups of slits. The plurality of linearly and angularly offset groups of slits are preferably linearly and angularly offset from each other in two dimensions.

A primary object of the invention is to provide an x-ray image from an x-ray source produced by a beam of electron magnetically deflected to sequentially intersect with a line target.

Another object of the invention is to provide a variety of x-ray images with a minimum number of detectors.

Yet another object of the invention is to automatically increase the incident x-ray flux (by increasing the "dwell time" of the x-ray beam) on portions of the object which are thicker than the average thickness of the object, to automatically decrease the flux where the object is thinner than the average thickness, and to automatically ignore the regions of the object space which contain no material.

Still another object of the invention is to provide stereoscopic views.

Yet another object of the invention is to provide x-ray viewing using only one detector per view.

A primary advantage of the invention is the relative ease of providing multiple views of the object including scatter views.

Another advantage of the invention is its adaptation to three-dimensional (stereoscopic) viewing of the object.

Still another advantage of the invention is its improved cooling of electron beam power at the x-ray source.

Yet another advantage of this invention is the simplification in X-Ray target design which the decreased electron beam density on target affords.

Yet another advantage of the invention is its production of better delineated image formation.

Another advantage of the invention is its ease of providing improved radiation shielding.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

Figures 1A, 1B:
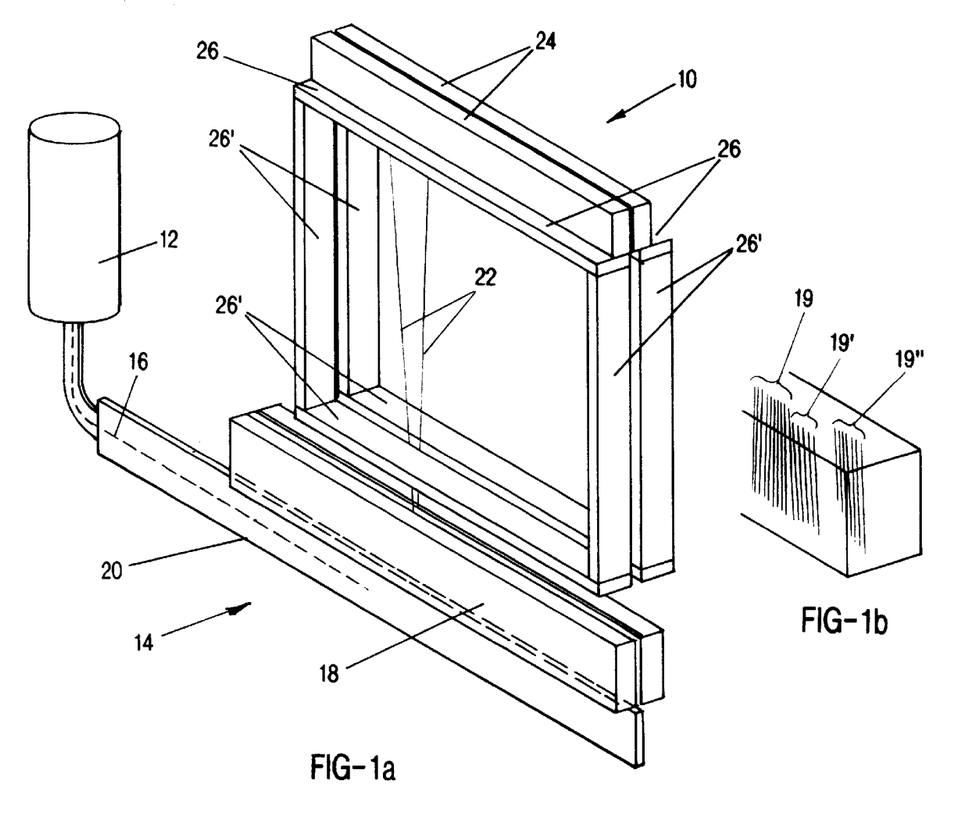
FIG. 1(a) is a schematic perspective of the preferred apparatus of the invention.
FIG. 1(b) is a perspective cross-section of the portion circled in FIG. 1(a).

With reference to the Figures, particularly FIG. 1, therein is depicted the preferred MeVScan apparatus 10 of the invention. Apparatus 10 is generally comprised of high voltage electrostatic generator/particle accelerator 12 and scanner 14, which also comprises radiation shielding as required (not shown).

Figure 2:
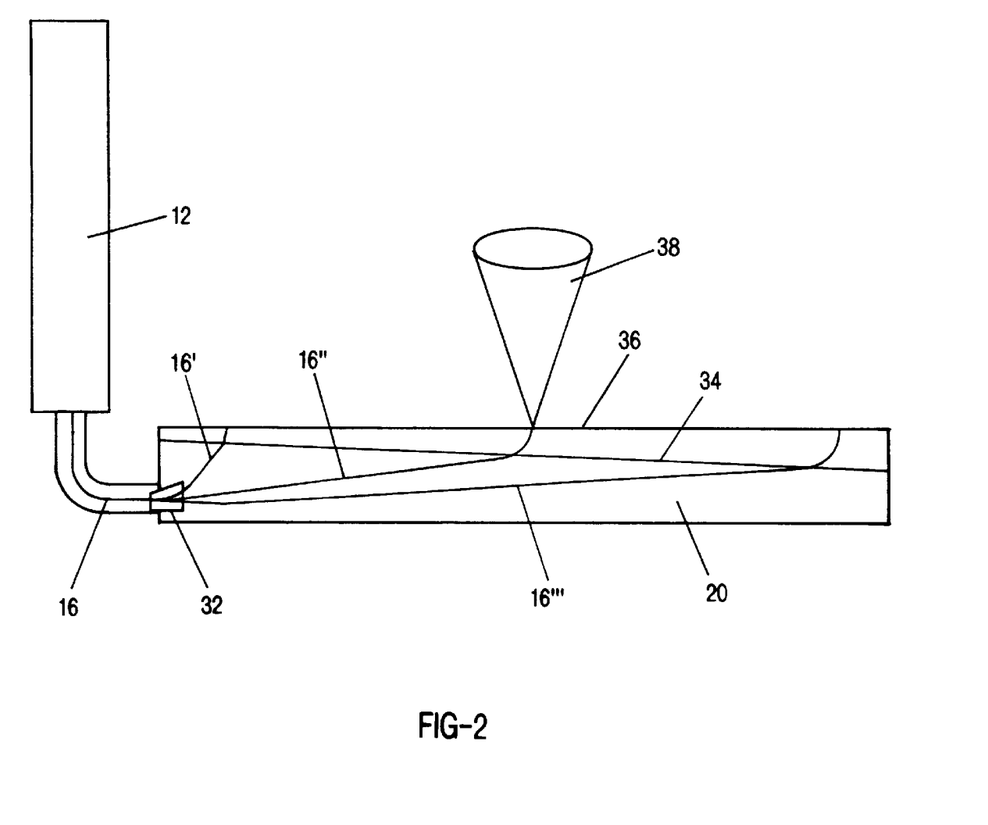
FIG. 2 is a cross-section of vacuum chamber 20.

As shown in FIGS. 1(a) and 2, generator 12 produces a high energy electron beam 16. Generator 12 may comprise the nested high voltage generator/particle accelerator disclosed in U.S. Pat. No. 5,124,658, issued Jun. 23, 1992, or any other suitable electrostatic generator/accelerator known to those skilled in the art.

Electron beam 16, preferably of several million electron volts, is introduced into elongate vacuum chamber 20 through preliminary bending magnet 32, as shown in FIG. 2. Controllable or programmable final bend magnet 34 "bends" electron beam 16 into a plurality of preselected, controlled trajectories, for example, 16', 16" and 16'". Final bend magnet 34 also acts to maximize radiation in order to offset the Bremstrahlung effect. Other means for controlling the trajectories of electron beam 16 well known to those skilled in the art can be utilized.

Figure 4A:
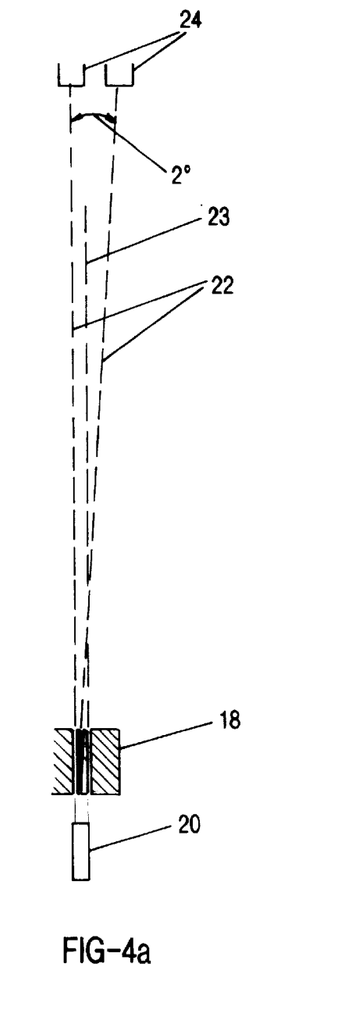
FIG. 4(a) is a side view and cross-section of the preferred apparatus of the invention.
Figure 4B:
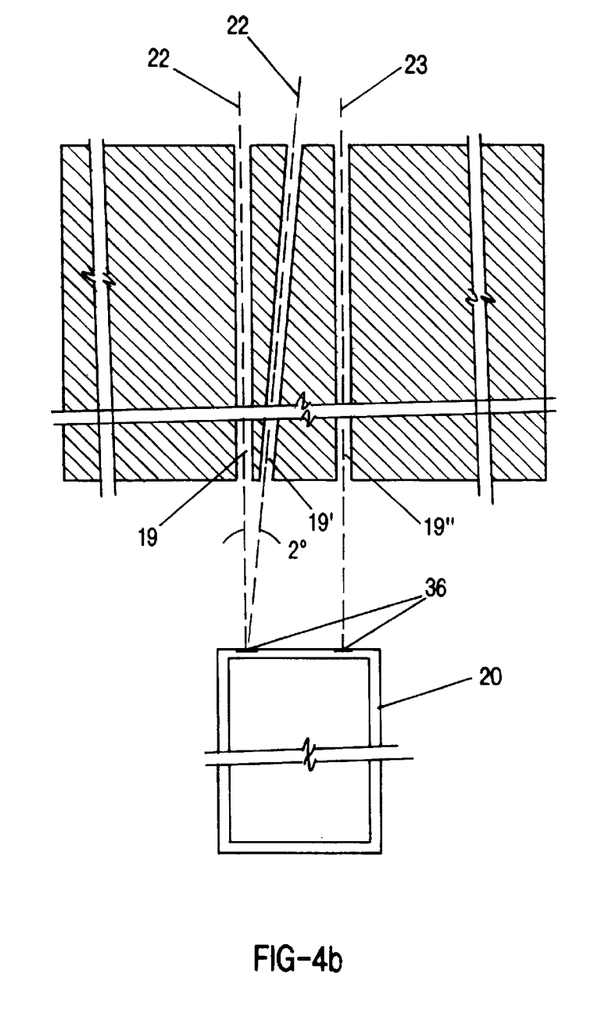
FIG. 4(b) is an enlarged view of the circled portion of FIG. 4(a)

Electron beam trajectories 16', 16" and 16'" impact x-ray conversation target 36, shown in FIGS. 2 and 4(b) thereby converting electron beam 16 into a plurality of photon beam cones 38. Photon beam cones 38 then, sequentially intercept collimator 18, the object to be imaged (not shown); are detected by transmission detectors 24, and ultimately produce the preselected desired images.

Typically, x-ray conversion target(s) 36, shown in FIGS. 2 and 4(b) comprise x-ray emitter material, for example, molybdenum or tungsten. A less expensive target material such as gold-plated aluminum can be used in this invention. Other emitter materials will suggest themselves to those skilled in the art.

Figure 3:
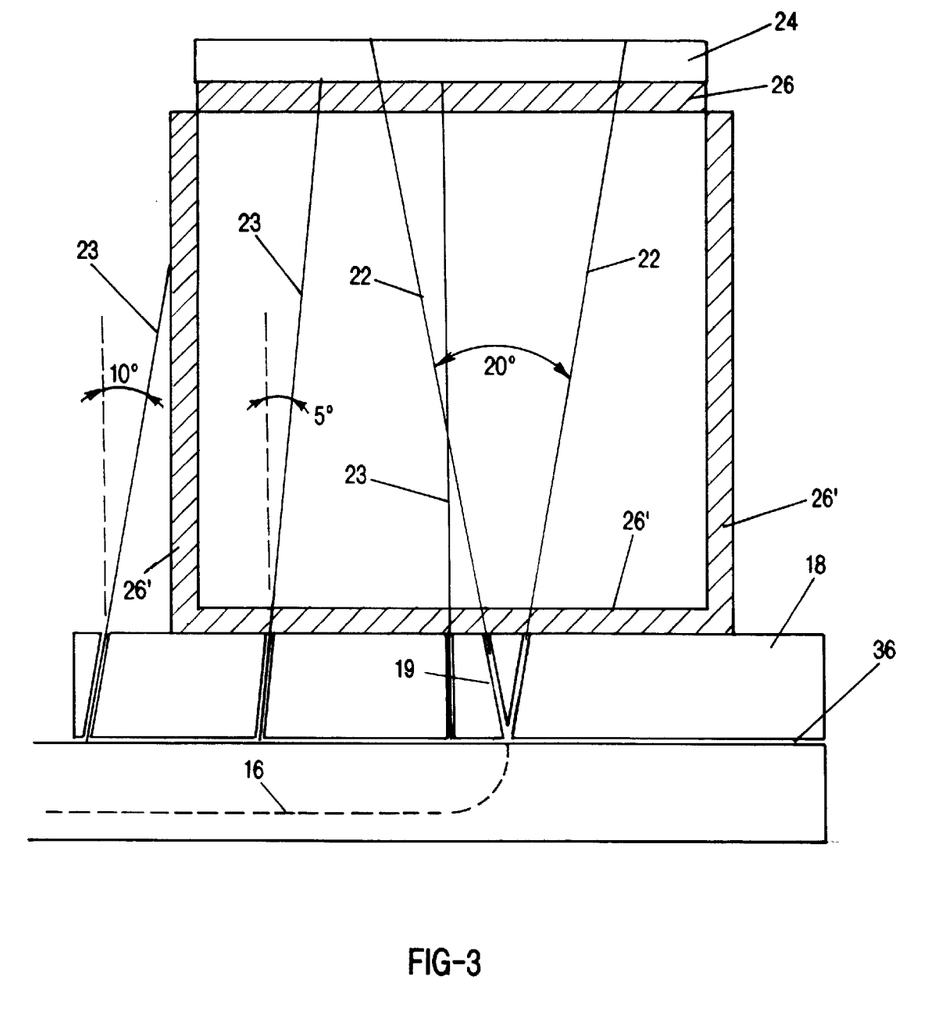
FIG. 3 is a front view of the preferred apparatus of the invention.

Photon cones 38 next, in the programmed sequence, intersect stationary collimator 18, as shown in FIGS. 1(a) and 1(b), 3 and 4(a) and 4(b). Stationary collimator 18 comprises a brass or other x-ray opaque material. Stationary collimator 18 also comprises a plurality of channeling slots or slits 19 for passage of photons. As best shown in FIG. 1(b), in the preferred embodiment, slits 19 are grouped into an exemplary plurality of slit arrays: 19, 19' and 19". Slit arrays, 19, 19' and 19", as shown, are offset from each other linearly and angularly in two dimensions. As best shown in FIGS. 3 and 4(a), slit arrays 19, are angularly displaced by 20° when viewed along an end plane normal to the longitudinal axes of vacuum chamber 20 and transmission detectors 24 (FIG. 4(a)); slit arrays 19 and 19' are angularly offset by 20° when viewed in a plane parallel to the longitudinal axes of vacuum chamber 20 and transmission detectors 24 (FIG. 3). Please note that the 20° as shown in FIG. 3 is in a different plane.

It is emphasized that any desired combination of slits and slit arrays may be used, depending upon the images desired. Further, the slits and slit arrays may be positioned in any desired configuration, again depending upon the result, subject only to the imagination and knowledge of those skilled in the art.

This particular slit array configuration permits the production of pencil-like transmission beams 22 through slit arrays 19 and 19', and scatter beam 23. Because of their offset, pencil-like transmission beams 22 can produce two images in "stereoscopic" fashion during a single scan of vacuum chamber 20. Transmission beams 22, then impact transmission detectors 24, and ultimately create the preselected or desired images. In this embodiment, a scattered beam is one which results from scattering (such as the process of Compton scattering) of the incident X-ray in medium of the object being inspected. This scattered X-ray is indicative of the density or type of material in the first few inches of the surface of the object being inspected, and scatter images of several types can be constructed as indicated below.

A subsequent scan along the displaced scatter x-ray target converter line (FIG. 4(b)) produces scatter beam 23 and two simultaneous scatter images: left side and bottom and right side of the object; and the top of the object. Scatter beams 23 are of course detected in the various scatter detectors 26 and 26', of FIG. 3.

The key to forming two simultaneous transmission images is the maintenance of distinct x-ray paths in the stationary collimator 18, together with the positioning of the two transmission detectors 24 (although only one detector could be employed).

The formation of the image is determined by the correlation between the x-ray source position or equivalently, the electron beam impact position, the slits in the stationary collimator 18, and the signal from the detector 24. The x-ray density for a given line through the object is proportional to the detector 24 output at the time at which the electron beam is at a position defined by the given line through the object. This line defines a single pixel of the image. The intensity of X-radiation is measured at that time, and the ratio of the intensity with the object in place to the intensity without the object in place is a measure of the total x-ray absorption through the line defined by the measurement object position and collimator 18. The measurement of X-ray absorption is made at each position where there is a collimator slit. The electron beam defines a line of pixels as it is scanned along the x-ray converter. The object is then moved along by a conveyer or other means, and the scan is repeated, thus producing a second line of pixels. A single collimator 18 may be used to produce multiple views by placing collimator slit arrays 19 at various lateral positions on the collimator.

Figure 5:
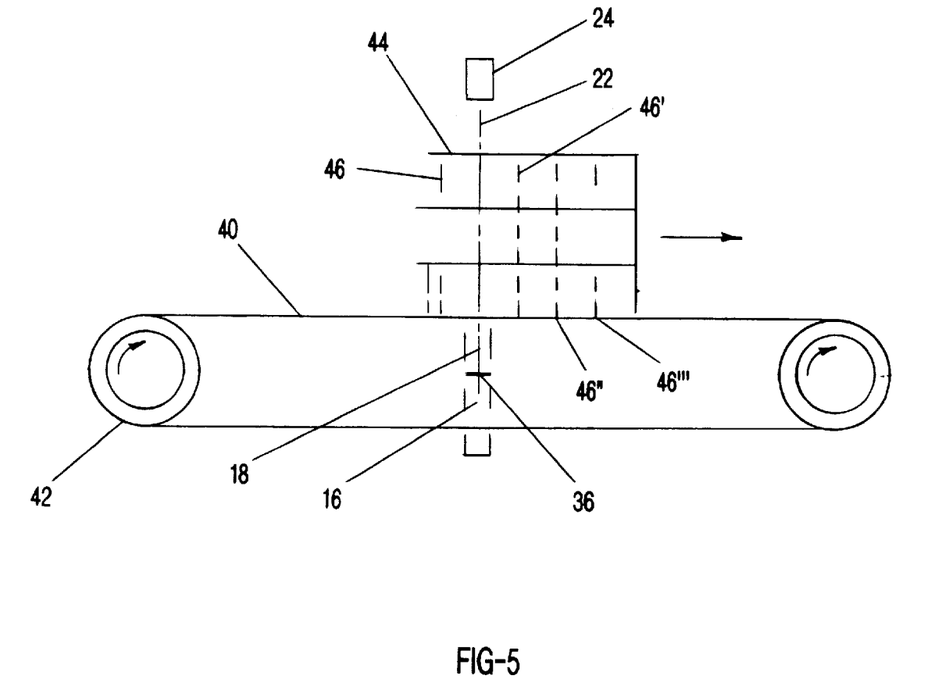
FIG. 5 shows a conveyor embodiment of the invention.

FIG. 5 illustrates the preferred conveyor MeVScan embodiment. Conveyor 40 is operated by conveyor motor 42 as shown. Object to be scanned 44 is moved by conveyor 40 and is transversely scanned by the MeVScan system as the object is continuously moved from one direction to the other (left to right in FIG. 5). Object 44 is irradiated as previously disclosed, by electron beam 16 to electron conversion target 36 and collimator 18. Object 44 is shown as three (3) boxes stacked on top of each other. As object 44 is moved, electron beam 16 and X-ray beam 22 are scanned, as shown, to detector 24, with each scan producing a row of pixels. Each scan provides a line of X-ray absorption data which is added to the image. X-ray scan locations 46, 46', 46" and 46'" are shown as dashed lines through object 44.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. Scanning apparatus comprising:
  a high energy electrostatic generator and particle accelerator for producing a high energy electron beam;
  at least one programmable magnet for pre-selectively varying the trajectory of said electron beam;
  a target for converting the electron beam into a photon beam;
  a stationary collimator comprising a plurality of groups of slits linearly and angularly offset from each other in two dimensions, for collimating said photon beam into a pencil beam or plurality of pencil beams; and,
  at least one transmission detector for detecting said collimated pencil photon beam, whereby a plurality of preselected images, including stereoscopic images, are thereby produced.

2. The apparatus of claim 1 further comprising an X-ray transmission detector for detecting backscattered X-rays whereby said backscattered images are converted into an image.

3. The apparatus of claim 2 wherein said preselected images and said backscattered images are produced simultaneously.

4. The apparatus of claim 1 further comprising a means for moving the object to be scanned in a predetermined direction and speed.

5. A high energy scanning method comprising the steps of:
  a) producing a high energy electron beam;
  b) converting the electron beam into a photon beam;
  c) collimating the photon beam and thereby producing a preselected pattern of linearly and angularly offset pencil-like photon beams and
  d) detecting the pencil-like photon beams, whereby a plurality of preselected images, including stereoscopic images, are produced.

6. The method of claim 5 wherein the step of producing a high energy electron beam further comprises the step of providing a high energy electrostatic generator and particle accelerator.

7. The method of claim 5 wherein the step of converting the electron beam into a photon beam further comprises the step of pre-selectively varying the trajectory of the electron beam.

8. The method of claim 5 wherein the step of converting the electron beam into a photon beam further comprises the step of providing an X-ray conversion target.

9. The method of claim 5, wherein the step of converting the electron beam into the photon beam further comprises the step of providing a target of gold-plated on aluminum.

10. The method of claim 5 wherein the step of collimating the photon beam further comprises the step of providing a stationary collimator having a plurality of slits for producing the pencil-like photon beams.

11. The method of claim 10 wherein the step of providing a stationary collimator having a plurality of slits further comprises the step of providing a plurality of linearly and angularly offset groups of slits.

12. The method of claim 11 further comprising the step of providing a plurality of linearly and angularly offset groups of slits offset from each other in two dimensions.

13. The method of claim 5 further comprising the step of detecting backscattered X-rays whereby backscattered images are produced.

14. The method of claim 13 wherein the plurality of preselected images and backscattered images are produced simultaneously.

15. The method of claim 5 further comprising the step of moving the object to be scanned in a predetermined direction and speed.

16. High energy scanning apparatus comprising:
  means for producing a high energy electron beam;
  means for converting said electron beam into a photon beam;

means for collimating said photon beam and thereby producing a preselected pattern of linearly and angularly offset pencil-like photon beams and means for detecting said pencil-like photon beams, whereby a plurality of preselected images, including stereoscopic images, are produced.

17. The apparatus of claim 16 wherein said means for producing a high energy electron beam comprises megavolt electrostatic generator and particle accelerator means.

18. The apparatus of claim 16 wherein said means for converting said electron beam into a photon beam further comprises means for preselectively varying the trajectory of said electron beam.

19. The apparatus of claim 16 wherein said means for converting said electron beam into said photon beam comprises a tungsten emitter.

20. The apparatus of claim 16 wherein said means for converting said electron beam into said photon beam comprises a gold-plated aluminum emitter.

21. The apparatus of claim 16 wherein said means for collimating said photon beam comprises stationary collimator means having a plurality of slits for producing said pencil-like photon beams.

22. The apparatus of claim 21 wherein said plurality of slits further comprises a plurality of linearly and angularly offset groups of slits.

23. The apparatus of claim 22 wherein said plurality of linearly and angularly offset groups of slits are linearly and angularly offset from each other in two dimensions.

* * * * *